United States Patent [19]

Shoher et al.

[11] 4,273,580
[45] Jun. 16, 1981

[54] REINFORCED JACKET CROWN AND METHOD OF CONSTRUCTION

[76] Inventors: Itzhak Shoher, 50 Shlomo Hamelech St., Tel Aviv; Aharon E. Whiteman, 13 J1 Perez St., Petach Tikvah, both of Israel

[21] Appl. No.: 26,785

[22] Filed: Apr. 4, 1979

[51] Int. Cl.³ .............................. C22C 5/02; B22F 7/08
[52] U.S. Cl. ..................................... 75/165; 75/0.5 R; 75/247; 433/207
[58] Field of Search ...................... 75/0.5 R, 253, 165, 75/172 R, 172 G, 173 R, 200, 201, 247; 228/122; 428/546, 552; 433/206, 207, 208

[56] References Cited

U.S. PATENT DOCUMENTS

| | | | |
|---|---|---|---|
| 2,654,945 | 10/1953 | Richardson | 75/247 |
| 3,450,545 | 6/1969 | Ballard | 75/0.5 R |
| 4,062,676 | 12/1977 | Knosp | 75/165 |
| 4,132,830 | 1/1979 | Tsai | 75/165 |
| 4,181,757 | 1/1980 | Youdelis | 75/165 |

Primary Examiner—T. M. Tufariello
Attorney, Agent, or Firm—Eugene Lieberstein

[57] ABSTRACT

The reinforced jacket crown of the present invention comprises an inner structure including a thin metal foil of platinum conforming in shape to the tooth preparation to be restored, at least one fired on coating of a composition of finely divided particles of from about 1 to 100% by weight of a noble metal halide in combination with from zero to 99% by weight of a noble based metal and a relatively thick fired on outer coating of dental porcelain.

10 Claims, 8 Drawing Figures

REINFORCED JACKET CROWN AND METHOD OF CONSTRUCTION

This invention relates to the field of dental restorations and more particularly to the porcelain jacket crown restoration and to a method for forming a porcelain jacket crown.

Dental porcelain, a conventional material composed of a mixture of feldspar, quartz and kaolin is commonly used in fabricating dental restorations, for example jacket crowns. The full porcelain or jacket crown is esthetically superior to all other crown restorations and is virtually impossible to visually distinguish from a natural tooth. Accordingly, it should be commonplace but is, in general, indicated for use only as a full coverage for an anterior tooth where esthetics is the prime consideration. The limited use of the porcelain jacket crown is attributable to its present method of construction with the strength of the jacket crown dependent upon the strength of the porcelain material composition. Porcelain is inherently structurally weak and fragile. In addition, the present method of construction requires a high degree of proficiency to establish accurate marginal fit and finish and to avoid poor seating of the crown occlusally relative to the preparation. An improper fit at the gigival margin results in a cement line which readily washes away inviting decay and loosening the crown attachment.

The more conventionally fabricated crown construction is the porcelain veneer cast metal crown. A relatively thick metal understructure is formed from casting an investment of a wax or plastic pattern from the prepared tooth. Dental porcelain is then applied in layers over part or all of the understructure and fired at high temperature to form a veneer. The metal understructure is preferably formed from a noble based metal or alloy predominantly of gold. The thickness of the cast metal understructure ranges from about 0.2 to 0.5 mm. A cast metal understructure is expensive and particularly so for a noble based metal composition. Moreover, since the bulk of the restoration should be no greater than that of the tooth structure which originally occupied the space, a thick metal understructure minimizes the permissible thickness for the translucent porcelain veneer. Furthermore, any exposure of the metal understructure will detract from the esthetics of the restoration.

The present invention concerns itself with overcoming the shortcomings of the conventional porcelain jacket crown construction. In the conventional process for preparing a porcelain jacket crown a platinum foil is swaged about the prepared die of the tooth to form a matrix upon which the porcelain may be fired. The foil is then removed before the crown is cemented to the tooth preparation. The primary object of the present invention is to provide a reinforced jacket crown having a high resistance to fracture comparable with or even greater than the conventional porcelain veneer cast metal crown.

In accordance with the present invention the jacket crown is formed as a composite body having an inner structure composed of a thin foil layer of material conforming in shape to the prepared tooth, with at least one intermediate layer of a predetermined material composition surrounding the foil core and fused to one face thereof at a predetermined elevated temperature and a relatively thick outer coating of dental ceramic material surrounding said inner structure and being bonded to the foil layer through the intermediate layer. The intermediate layer between the porcelain coating and the foil layer is formed from a finely divided particle composition comprising of from about 1 to 100% of a noble metal halide and from zero to 99% of noble based metal particles.

The porcelain jacket crown of the present invention eliminates the need for waxing, casting and machining the understructure for a cast metal crown, is at least as strong as a cast metal crown and may be prepared at a substantially lower fabricating cost relative to the cast metal crown. Moreover, any type of margin preparation is equally acceptable for use with the composite jacket crown of the present invention. In addition, the composite jacket crown of the present invention minimizes the need for substantial contouring of the tooth preparation and as such minimizes the potential for tissue disease.

Further objects and advantages of the present invention will become apparent from the following detailed description of the invention when read in conjunction with the accompanying drawings of which:

Figure 1:
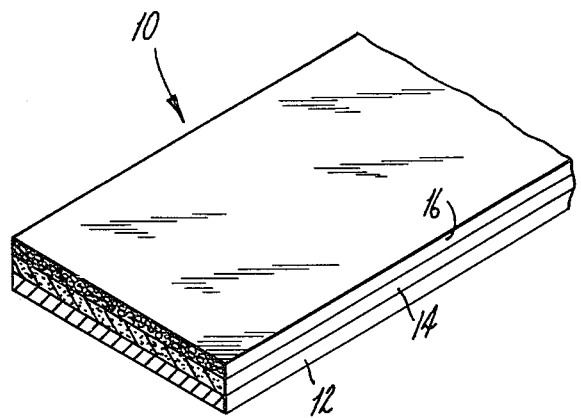
FIG. 1 is an enlarged perspective of a rectangular segment of the preferred metal foil starting material for forming the inner structure of the jacket crown of the present invention with one end shown in cross-section.

The preferred starting material is shown in FIG. 1 in the form of a preformed metal foil strip 10 of rectangular geometry. The preformed foil strip 10 includes a thin base metal layer 12 preferably of platinum or another high fusing temperature matal, a first coating 14 of a predetermined material composition bonded to the layer 12 at a first elevated temperature and a second coating 16 applied over the first coating 14. The coating 14 is composed of a finely divided metal particle composition comprising a halide of a noble metal in a range from about 1 to 100% by weight in combination with a noble based metal in a range from zero to 99% by weight. The preferred noble metal is selected from the group consisting of silver, palladium, platinum and gold with other noble metals such as indium, rhodium, osmium and iridium being less desirable. The halide is preferably selected from the group consisting of a chloride or fluoride, although a bromide or iodide may be used. The noble metal halide is a critical ingredient. Noble metal halides are commercially available in a granulated powder or crystalline form. For example, gold chloride is commercially available also as chlorauric acid ($HAuCl_4$) in a powdered crystal form. The shape or form of the finely divided particles are not essential to the present invention but should preferably be of a size below about 10 microns.

The noble based metal component of the coating 14 is preferably a gold based noble metal comprising at least about 50% by weight finely divided particles of gold with a remainder of one or more of other finely divided noble metal particles such as silver, platinum, palladium, rhodium and indium and may contain traces of preferably no more than a total of about 5% by weight of any one or more non-precious metals such as copper, zinc, iron, tin, cadmium, magnesium, germanium, manganese, cobalt and nickel. It should be understood that although a predominantly gold based noble metal is preferred because it provides a desirable background color the present invention is not to be construed as limited thereto. Noble based metal is defined for purposes of the present invention as a metal or metal alloy containing one or more noble metal constituents representing all or a relatively substantial proportion by weight of such metal or metal alloy. The average particles size for the noble based metal component is preferably below about 10 microns and may be in any desired form such as flakes, granules or powder.

The material composition of coating 14 is discussed in greater detail in a corresponding U.S. patent application Ser. No. 171,255 entitled Bonding Material And Method For Bonding A Ceramic To A Noble Based Metal At Elevated Temperature which is herein incorporated by reference.

It is essential to the present invention that the first coating 14 be sintered to the base metal layer 12 at an elevated temperature above at least about 1600° F. with the optimum sintering temperature lying in a range of between about 1875° F. to 1975° F. Within the optimum temperature range the first coating 14 is wetted uniformly over the full surface of the platinum layer 12. The sintering operation forms a clinically unbreakable bond between the coating 14 and the platinum layer 12. Although the sintering operation is preferably performed before the foil 10 is adapted to the die 18 it should be understood that the process of the present invention broadly encompasses applying and sintering the coating 14 to the platinum layer 12 after the latter is adapted to the die. In fact, the coating 14 may be sintered simultaneously with the firing of the porcelain outer layers. This, however, would limit the sintering temperature to that normally used for firing porcelain which lies in general between 1600°–1820° F.

The coating material 14 may be applied to the surface of the platinum layer 12 with or without a suitable binder. It is preferred, however, to suspend the coating material 14 in a carrying vehicle so that it may be readily applied by brushing, painting, dripping or spraying onto the platinum layer. Any suitable carrying vehicle, preferably one which will volatilize in the sintering process without a residue, may be used including known water detergents or an organic resinous or synthetic resinous medium thinned with a suitable solvent. When a binder is not used the coating material 14 may be simply sprinkled over the platinum foil layer 12. The coating material 14 may be built up into a layer of any desired thickness. It is, however, preferred that it be applied as a thin film in about the same thickness range as that of the thin platinum layer 12 which varies from about 0.0015 mm to 0.05 mm thick. There is, in fact, no limitation to the thickness of the layer of coating material 14 except as it relates to the physical and handling properties of the foil 10 after sintering. If the layer 14 is too thick it will make the foil 10 too rigid to adapt to the die.

Although the preformed foil 10 preferably includes a second coating 16; the second coating 16 is not essential to the invention. Moreover, the coating 16 may be applied over the first coating 14 after the foil is adapted to the die and thereafter sintered before or concurrent with the firing of the porcelain coating. The second coating 16 consists of a composition equivalent to the composition of coating 14 although not necessarily with the noble metal halide component and the noble based metal component in the same chosen proportion as coating 14. The coating material 16 may similarly be suspended in a carrying vehicle for controllably applying the material over the surface of the first coating 14. Application of the second coating 16 should be relatively uniform with a thickness equal to or less than the thickness of the first coating 14. The sintering operation for the second coating 16 should be conducted at a sintering temperature sufficient to convert the finely divided particle composition of coating 16 into globules or beads of substantially spherical geometry which are preferably irregular in size. The beaded particles have been shown to operate as stress breakers for increasing fracture resistance of the jacket crown to external forces. Optimum beading appears to occur at a temperature range between about 1775° F. to 1875° F. Sintering of the second coating 16 forms an unbreakable bond between the first and second coatings 14 and 16 respectively.

Figure 2:
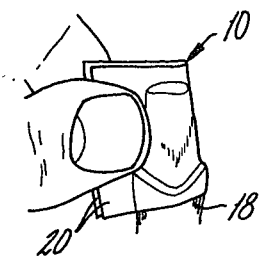
FIG. 2 shows a transparency of the metallic foil of FIG. 1 in the process of being hand molded about a die of the prepared tooth.
Figure 3:
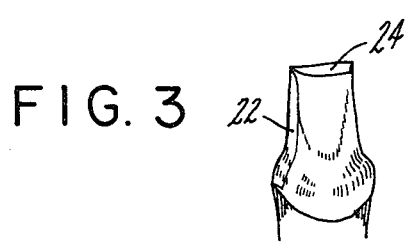
FIG. 3 shows the foil of FIG. 2 after it has been trimmed and finished.
Figure 4:
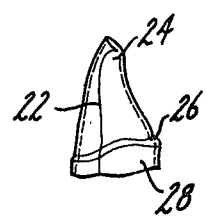
FIG. 4 is a further showing of the foil inner structure of the present invention after being removed from the die.
Figure 5:
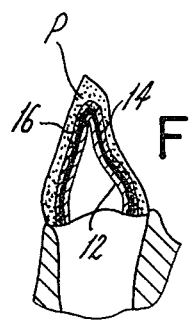
FIG. 5 is an illustration in cross-section of the porcelain jacket crown of the present invention for an incisor tooth with a conventional shoulder margin preparation.
Figure 6:
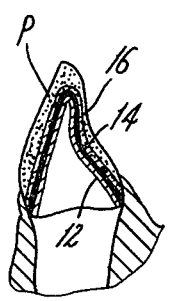
FIG. 6 is another illustration in cross-section of a porcelain jacket crown of the present invention for an incisor tooth similar to FIG. 5 with a conventional knife or feather edge margin preparation.
Figure 7:
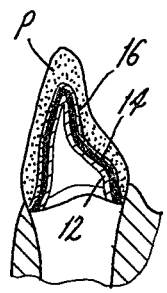
FIG. 7 is yet another illustration in cross-section of a porcelain jacket crown of the present invention for an incisor tooth with a conventional chamfered margin preparation.
Figure 8:
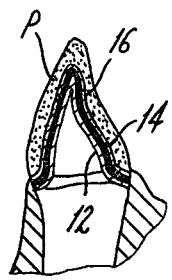
FIG. 8 is a still further illustration in cross-section of a porcelain jacket crown of the present invention for an incisor tooth with a more complex chamfered bevel margin preparation.

FIGS. 2 and 3 illustrate the sequence used to adapt the rectangular foil 10 to the die 18. The die 18 is conventionally prepared from an impression of the prepared tooth and is a replica thereof. The foil is wrapped tightly about the die 18 to form overlapping ends 20 which are trimmed down and folded over to form flaps 22 and 24. The foil 10 should also extend over the gingival margin 16 to form a skirt 28. The die 18 and foil 10 is then placed in a swaging device or pressure applied to the foil by hand to adapt it to the die 18. The foil 10 is then removed from the die 18 leaving a free standing structure, as shown in FIG. 4, over which any number of porcelain layers may be applied and fired for forming the jacket crown of the invention. Generally, three or more layers of varying dental porcelain composition starting with an opaque layer are built up and fired at temperatures in a range from about 1600° to 1820° F. Before firing the final glaze the extended skirt 28 is cut and the porcelain shaped and finished to the correct gingival margin of the prepared tooth.

After the final glaze the crown is ready to be inserted into the mouth and cemented to the tooth. The uncoated side of the platinum layer 12 is preferably roughened to firmly engage and contact the tooth preparation in the mouth. This roughness may be formed before or after adapting the foil 10 to the die by sandblasting or grinding one face of the platinum strip. Any conventional cement material may be used to cement the crown to the tooth preparation.

The jacket crown of the present invention is suited to all conventional gingival margin teeth preparations as illustrated in FIGS. 5 to 8. Any one of these types may be suitable for the whole circumferance of the crown or may be used with any other type. A comparative test was conducted to demonstrate the strength of the porcelain jacket crown of the present invention relative to a conventional porcelain to cast metal crown. An upper central incisor foil crown was formed in accordance with the teachings of the present invention and secured to a metal base. A metal pin was positioned in contact with the incisal edge of the crown. A 100 gram iron cylinder was dropped from 20 cm over the pin without causing any apparent damage. The weight was then dropped from 40 cm over the pin. This causes a limited area of porcelain breakage. A similar test was conducted with a conventionally prepared porcelain to cast metal crown. The 100 gram weight was dropped from 20 cm over a pin contacting the same incisal edge position. The drop of the weight caused a large part of the buccal porcelain to break off. In each case the porcelain was an identical ceramic porcelain composition from Ceramco.

What is claimed is:

1. A reinforced porcelain jacket crown restoration comprising a composite body including a thin metal foil of platinum conforming in shape to the tooth preparation to be restored, at least one thin intermediate coating of a predetermined composition of finely divided particles bonded to said thin metal foil at an elevated sintering temperature above at least 1600° F.; said composition comprising, from about 1 to 100% by weight of a noble metal chloride with said noble metal being selected from the group consisting of gold, silver, palladium and platinum in combination with from zero to 99% by weight of a gold based noble metal; and a relatively thick fired on outer coating of dental porcelain.

2. A reinforced jacket crown as defined in claim 1 wherein said thin intermediate coating is uniformly wetted to said thin platinum foil at a first sintering temperature between about 1875° F. to 1975° F.

3. A reinforced jacket crown as defined in claim 2 further comprising a second thin coating equivalent in composition to said intermediate coating and being bonded thereupon at a sintering temperature to form beaded particles of irregular size.

4. A reinforced jacket crown as defined in claim 3 wherein said finely divided particle composition is suspended in a volatizing carrying vehicle.

5. A reinforced jacket crown as defined in claim 3 wherein said noble based metal particles comprises at least about 50% by weight finely divided gold particles in combination with from zero to 45% finely divided noble metal particles selected from the group consisting of silver, platinum, palladium, rhodium and indium.

6. A method of constructing a reinforced porcelain jacket crown comprising the steps of:

coating the surface of a platinum metal strip with a predetermined material composition of finely divided particles of from about 1 to 100% by weight of a noble metal halide in combination with from zero to 99% by weight of noble based metal particles;

sintering said coated strip at an elevated temperature in a range of between about 1875° F. to 1975° F.

forming an inner structure for said crown by adapting said strip to a die of a tooth preparation to be restored; and firing a predetermined number of porcelain layers over said inner structure to form a relatively thick outer coating.

7. A method as defined in claim 1 further comprising the step of applying a second coating of said predetermined material composition upon said sintered coated strip and sintering said second coating in a temperature range between about 1775° F. to 1875° F.

8. A method as defined in claim 7 wherein said second coating is applied before said inner structure is formed.

9. A method as defined in claim 7 wherein said second coating is applied after said inner structure is formed.

10. A method as defined in claim 6 wherein said noble metal halide is a gold based noble metal chloride.

* * * * *